United States Patent [19]

Deutsch et al.

[11] Patent Number: 4,824,371
[45] Date of Patent: Apr. 25, 1989

[54] RETENTION DEVICE FOR DENTURES AND THE LIKE

[75] Inventors: Allan S. Deutsch; Barry L. Musikant, both of New York, N.Y.

[73] Assignee: Essential Dental Systems, Inc., New York, N.Y.

[21] Appl. No.: 942,761

[22] Filed: Dec. 17, 1986

[51] Int. Cl.$^4$ .......................................... A61C 13/235
[52] U.S. Cl. .................................................. 433/189
[58] Field of Search ............... 433/189, 173, 174, 220, 433/221

[56] References Cited

U.S. PATENT DOCUMENTS

| | | | |
|---|---|---|---|
| 2,732,621 | 1/1956 | Pelzmann | 433/189 |
| 3,646,676 | 3/1972 | Mitchell | 433/189 |
| 4,184,252 | 1/1980 | Krol et al. | 433/189 |
| 4,202,097 | 5/1980 | Erlich-Deguemp | 433/189 |
| 4,431,419 | 2/1984 | Portnoy | 433/189 |

FOREIGN PATENT DOCUMENTS 2308348 12/1976 France ................................ 433/189

Primary Examiner—John J. Wilson
Assistant Examiner—Adriene J. Lepiane
Attorney, Agent, or Firm—Bauer & Schaffer

[57] ABSTRACT

A releasable magnetic retention device having two opposed substantially like units each of which has a relatively small permanent magnet of opposed poles, one pole of which is utilized with a conductor of low coercivity material to form a larger magnetic flux field in the conductor so that when the two like units are placed in magnetic attracting relation the two conductors complete a strong enlarged magnetic flux path between them to releasably retain the units together.

21 Claims, 1 Drawing Sheet

RETENTION DEVICE FOR DENTURES AND THE LIKE

This invention relates to a releasable magnetic retention device that is more particularly directed to the retention of dentures, although not specifically limited thereto.

Magnetic denture retention devices have been popularly employed because of their ability to release the retained denture for easy removal at night for cleaning and to effect necessary repairs without disturbing other teeth or orthodontic structures that are contained within the mouth. Typical recent examples of such magnetic retention devices are disclosed in U.S. Pat. Nos. 4,214,366 and 4,431,419, each of which utilizes a tooth implant as an anchor for a part of the retention deice. Each such device, however, teaches the use of a single magnet to complete a magnetic flux path that is readily broken in response to lateral or other separating forces applied to the denture.

The present invention provides a magnetic retention device that is unusually well adapted for dentures because of its ability to produce at least two large magnetic flux fields of opposite polarity larger than their respective magnets. The flux fields ar concentrated in and directed along conductors of low coercivity material so that when the two flux fields are in attracting relation, they produce an extremely strong combined magnetic flux path that is completed across them. The completed combined flux path is so strong and greatly increased in size from that known heretofore that it is now possible to materially reduce the size and weight of the present retention device, relative to that which has been known before or previously used. This enables a reduction in the weight of the denture and improves the comfort to the wearer.

The above description, as well as further objects, features and advantages of the present invention, will be more fully appreciated by reference to the following detailed description of a presently preferred, but nonetheless illustrative, embodiment in accordance with the present invention when taken in conjunction with the accompanying drawings wherein:

DESCRIPTION OF THE INVENTION

Figure 4:
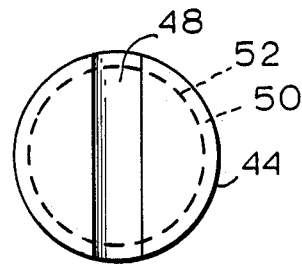
FIG. 4 is a top view of FIG. 3.
Figure 3:
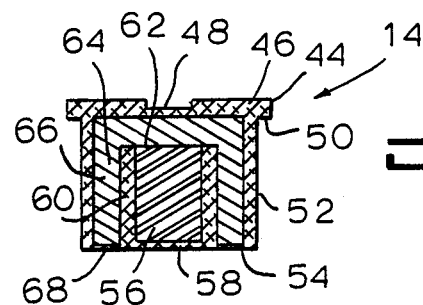
FIG. 3 is a vertical cross-section of another retention unit of the present invention.
Figure 1:
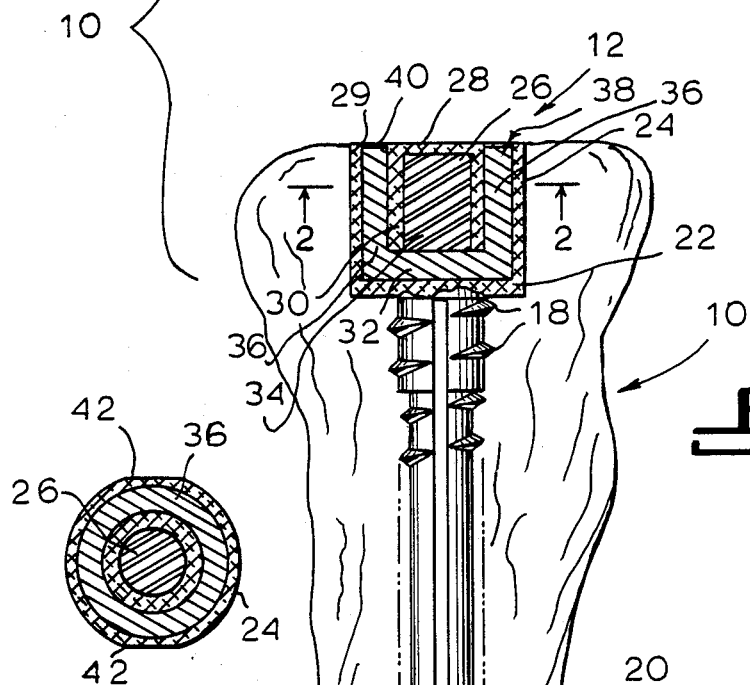
FIG. 1 is a partial vertical cross-section of a tooth having one unitary part of the retention device implanted therein and constructed according to the teaching of the invention.
Figure 2:
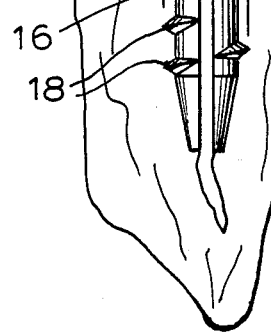
FIG. 2 is a cross-section of the retention unit shown in FIG. 1 taken along lines 2—2 thereof.

Referring now to the drawing, the releasable magnetic retention device of the present invention is generally illustrated in FIGS. 1 and 3 by the bracket 10. The device 10 comprises two units, one of which is generally identified in FIG. 1 by the numeral 12 and the other is generally identified in FIG. 3 by the numeral 14.

The retention unit 12 is shown formed as a proximal part of a dental post generally identified by the numeral 16. The dental post may be of any desired configuration and construction. Since its operative structural details form no part of the present invention the same is not disclosed herein other than to note that the same is threaded as at 18. Hence, the details of the dental post hereshown are not to be deemed to be a limitation upon the scope of the present invention. The thread 18 is provided to enable the dental post to be threaded into the dentin or root canal of a tooth 20.

The retention unit 12 shown in FIG. 1 is formed as a singular monolithic part of the dental post 16. This illustration should not be construed as a restriction upon the scope of the present invention since it is possible that the unit 12 may be formed as a unitary structure completely separate from any dental post. When so formed the unit 12 may be used as an implant in a denture or in any other support or bony structure of the mouth or with any other support to which the present retention device may be mounted. The unit 12 comprises a holder that is formed substantially cup-shaped having a base 22 that merges continuously and uninterruptedly with an upstanding circular wall 24. The wall 24 terminates the open end of the holder in a ring-shaped opening that enables the holder 22 to function as a housing.

The holder is made of a non-magnetic non-corrosive material. Titanium has been found to be an unusually suitable material for this purpose and is, therefore, preferred for its light weight, its easy machinability, and its non-magnetic and non-corrosive characteristics. This is especially important when the holder is intended to be formed as a unitary, monolithic part of the dental post 16 and thus must be machined during the machining of the dental post and the threads 18 thereon. The lightness of the titanium material and its non-corrosiveness are also important in reducing the weight that must be contained within the mouth of the wearer and a material of long life, lasting at least for the life of the wearer, free of corrosion.

Housed within the holder is at least one or more disk-shaped or circular permanent magnets 26. Each of the magnets will have opposite polarity. For ease of explanation, only one of such magnets is illustrated in the drawing. As the description proceeds, however, it will become apparent that the number of the magnet(s) 26 used and their shape is but a matter of choice depending upon the strength of the magnetic field that is desired to be produced. In practice, the magnet is preferably made of relatively new magnetic alloy of cobalt and Samarium. Although this alloy is preferred, other permanent magnets of other materials may also be used. This relatively new alloy known as "$CO_5Sm$" has very high coercivity and produces very high magnetic fields, especially for the relatively small size and weight of the magnet.

The magnet 26 is located within the holder such that its magnetic pole facing the proximal or open end of the housing is depressed thereinto and is covered by an inverted substantially cup-shaped insular having an insulating covering base 28. The proximal surface of the covering base 28 is in horizontal alignment with or slightly below the rim 29 of the ring-like rim end of the wall 24. Formed inseparable with to extend along the adjacent side wall of the magnet 22 is an insulating side wall 30 of the magnet insulator. Once again the insulator cup 28, 30 is preferably made of light-weight, non-corrosive, non-magnetic material as titanium. Once again although titanium is preferred for the reasons noted above, other materials or combinations of materials meeting these criteria may also be usable.

It is noted that the base 28 and side 30 insulate the respective covered proximal pole and covered side of the magnet 26 while leaving the opposite distal magnetic pole 34 of the magnet completely free and exposed so that it may be in contact with a base 32 of a magnetically conductive member of low coercivity characteristics. The magnetically conductive member is also substantially cup-shaped with its base 32 in magnetic touching contact with the exposed distal magnetic pole 34 of the magnet 26 and with its circular upstanding wall 36 surrounding the insulator side wall 30. The upstanding wall 36 and the base 32 of the conductive member are continuous and formed as a single structure so as to assure the continuity of the flow of magnetic flux completely through the member from the point of contact with the magnetic pole 34 to its terminating ring-shaped rim 38 that opens at the proximal end of the unit 12.

The magnetic conductive member may be of any magnetic material of low coercivity. It is preferred that the same be formed of Series 400 ferromagnetic stainless steel. The Series 400 ferromagnetic stainless steel material exhibits the ability to provide a closed directed pathway for the magnetic flux produced at the contacted magnetic pole 34. This closed pathway is further enhanced by the enclosure and confinement of the base 32 and the side wall 36 by the inner insulator wall 30 and by the walls 22 and 24 of the outer insulator holder. Although not required, the magnetic conductor member is bonded in any convenient manner to the inner insulator and outer holder to fix these members relative to each other and to further confine the magnetic flux for its directed and confined flow along the pathway formed by the continuous inseparable base 32 and side wall 36.

The proximal open end 36 of the magnetic conductive member may be attractively covered with a layer of gold foil 40 or other highly conductive non-corrosive material that will not interfere with or inhibit the flow of magnetic flux from beyond the open end 38. The outer peripheral surface of the side wall 24 of the holder is conveniently provided with a set of diametrically opposed flats 42 for rotating engagement by the jaws of a wrench or like tool that may be used to thread the threaded post 18 into any suitable support in the mouth including, without limitation, into the dentin or root of a tooth.

The oppositely facing retention unit 14 is of substantially the same construction, size, and shape as is the aforedescribed unit 12. The unit 14 includes an enlarged flange 44 that may be formed as an integral part of the non-magnetic, non-corrosive, light-weight holder 46 that may also be of titanium or other material having similar characteristics. To enable the unit 14 to be used with and as a physical part of a denture, it is shown provided with an anti-rotation groove 48 that may extend diametrically across the top of the enlarged flange 44.

When the unit 14 is mounted in a denture, the denture is formed over and about either all or part of the overextending lip 50 of the flange 44 and fits fully within the groove 48. This relationship locks the unit 14 and denture together from relative rotation and also from longitudinal separation. The flange 44 and groove 48 have been found to be simple, yet effective, but by no means should they be limiting upon the scope of the invention. Other structures may be used to effect the same result.

The holder 46 is substantially cup-shaped having the outer wall 52 that is hereshown to be a continuation of the flange 44 that functions as the cup base. Like the holder of the unit 12 the holder 46 terminates in an open ended circular or ring-shaped rim 54. Since the side walls 24 and 52 are of substantially equal size, their rims will mate in matching contact when the same are positioned against or adjacent to each other. The holder 46 functions as a housing to hold one or more permanent magnets 56 therein. The single magnet 56 shown in FIG. 3 has opposed magnetic poles and may be of the same preferred material as that described with respect to the magnet 26, although it is not limited to the use of the specific alloy as previously described.

The proximal pole of the circular permanent magnet 56 is insulated fully by a substantially cup-shaped insulator having a pole insulating base wall 58 and a continuously, uninterrupted side wall 60 that extends fully along the side of the magnet 56 toward the distal end magnetic pole 62. The insulating side wall 60 leaves the magnetic pole 62 fully exposed for intimate and direct magnetic contact with a substantially cup-shaped magnetically conductive member of low coercivity that may be similar to that in appearance and construction and of the same material as the magnetic conductive member of the unit 12.

The base wall or side 64 of the conductive member is in direct contact with the distal magnetic pole 62 to conduct the flow of magnetic flux therefrom. In the same manner as the conductive member of the unit 12, it too conducts the magnetic flux from the contacted magnetic pole 62 along its base and along its side wall 66 that is insulated and enclosed by the wall 52 of the holder and 60 of the magnet insulator. As in the unit 12, the side wall 66 may extend to the open ring-shaped rim end 54 of its respective holder or it may be slightly recessed therefrom to be covered by a magnetic conductive layer 68 of non-corrosive material as gold or the like.

Once again, because the retention units 12 and 14 are substantially the same in size, shape, and structural detail, the holder 46 and insulator 58, 60 may be of the same material as the corresponding structural members of unit 12. The low coercivity magnetic conductive member 64, 66 may also be of the same Series 400 ferromagnetic stainless steel as the corresponding member of the unit 12. The size and shape of the holders, their respective magnetic conductive members, and their respective magnets will be substantially the same such that when they are placed in face-to-face relationship as shown in FIGS. 1 and 3, their proximal ends will match and mate with each other when the same are properly aligned. This will enable the ends of each of the magnetic conductive members of both units 12 and 14 to be in circular facing, rim-to-rim mating alignment.

It will be recognized that even though the present invention has been described for use with a denture, it may have general utility with other mechanisms. It should also be obvious that the strength of the magnetic fields of one of the units may be changed with respect to that of the other since the same is within the scope of this invention. For certain uses it may be desirable to increase the magnetic field of one of the units or decrease the magnetic field of the other of the units so as to effect a release of the units.

In practice, the unit 12 may be threaded into a tooth or other mouth support by rotation of the same by a wrench, or the like, applied to the flat surfaces 42. The unit 14 may be implanted in a denture in a manner previously described so that it is fixed to the same against longitudinal displacement therefrom and rotation relative thereto. The units 12 and 14 should be longitudinally aligned as closely as possible with respect to each other so that the circular ring-shaped rim ends of their respective magnetic conductive members are also in alignment with each other.

It should be noted that the non-insulated exposed distal magnetic poles 34 and 62 of the respective units 12 and 14 should be of opposite magnetic polarity so as to effect an attraction between their respective units. If they are of like magnetic polarity, the retention units may be used in an opposite manner to repel and separate the units or denture from the dental post.

The exposed poles 34 and 62 produce attracting magnetic fields in their respective magnetic conductive members when they are of opposed polarity. The separate magnetic flux fields flow along and about the circular side walls 38 and 66 of their respective magnetic conductive members to produce a circular encompassing magnetic field of greater area than that which would be produced by the respective magnetic poles alone.

The unique arrangement of insulating the magnetic conductive members between the outer walls of the respective holders and the inner walls of the inner magnet insulators serve to restrict and inhibit the magnetic flux from straying outside of the path formed by the circular walls 36 and 66. This results in shielding the circular walls and in forming a closed path that directs the magnetic flux from the magnetic poles 34 and 62, substantially undiminished, along the length of the walls to their mating aligned circular ring-shaped rims. When the two retention units are positioned sufficiently close to attract each other, the opposite attracting magnetic flux paths will be completed across the, circular ring-shaped rim ends of the two magnetic conductive members to form a very large area of strong magnetic attraction between them.

The strength of the magnetic retention effected by the attraction of the units 12 and 14 is enhanced by the fact that both units produce magnetic flux of opposite attracting polarity that is concentrated at the circular ring-shaped rims of their respective magnetic conductive members of low coercivity. The retention effected by the present invention is releasable when a separating force is applied to one or both of the units in excess of the combined strength of the magnetic fields.

It is noted that the walls of the non-magnetic holder of each unit also shield the overall structure of its respective unit from nearby or surrounding magnetically attractive materials. Thus, the holder confines the magnetic flux to the path formed by its respective magnetic conductive member. This reduces the possibility of producing stray magnetic flux paths that may have an adverse or unfavorable effect upon the metals or other magnetically attractive structures that may be present in nearby teeth or orthodontic devices. The result is that the magnetic flux paths are concentrated and effectively directed to flow along their closed pathways from which the same cannot stray but must exit at the ring-shaped rims to complete the magnetic attraction between the units.

While there have been shown and described and pointed out the fundamental novel features of the invention as applied to a preferred embodiment thereof, it will be understood that various omissions and substitutions and changes in the form and details of the device illustrated and in its operation may be made by those skilled in the art without departing from the spirit of the invention. It is the intention, therefore, to be limited only as indicated by the scope of the claims appended hereto.

What is claimed is:

1. A releaseable retention device comprising a pair of cylindrical permanent magnets each having poles of opposite polarity at each end and set within a respective holder such that they may be arranged facing end to end, each of said holders comprising a pair of magnetically insulating components one inverted within the other, the inner component covering the facing end and the side walls of said permanent magnet, the outer component being spaced from the inner component and the other end of said permanent magnet; a body of low coercivity magnetic material interposed between said inner and outer components and surrounding the inner component in contact with the other end of said magnet, said body being open at the facing end of said holder; each of said permanent magnets being arranged in its respective holder so that the polarities at the ends of one permanent magnet are opposite to the polarities at the corresponding ends of the other permanent magnet, said low coercivity magnetic material in each holder forming an axial magnetic flux path of opposite polarity toward the facing end of its respective holder; said flux paths being co-relative to each other to close the magnetic field between the holders when said holders are in end to end proximity to each other to thereby releaseably retain said holders together.

2. A releasable retention device as in claim 1,
   each said low coercivity magnetic body terminating in a ring shape at the open end of its respective holder,
   and each said low coercivity magnetic body being of substantially equal size to complete the magnetic flux paths between said magnets of said two holders.

3. A releasable retention device as in claim 2, wherein said holder is of a non-magnetic and non-corrosive material.

4. A releasable retention device as in claim 3,
   said non-corrosive material being titanium.

5. A releasable retention device as in claim 1, said low coercivity magnetic body being of a ferromagnetic stainless steel.

6. A releasable retention device as in claim 1,
   each said magnet being of a cobalt samarium alloy.

7. A releasable retention device as in claim 1,
   at least one of said holders being unitary with and forming a monolithic part of a dental post and the other of said holders being embedded in a denture.

8. A releasable retention device as in claim 7,
   said holder that is embedded in a denture having means thereon for non-rotatable engagement with the denture,
   and said holder forming a part of a dental post having means for moving the dental post into engagement with a tooth.

9. In a denture retention device,
   a pair of facing magnet units one for retention in the denture and the other for retention in a tooth or other support,
   said magnet units being substantial duplicates of each other with each of said magnet units comprising:
   a circular cup-shaped magnetic conductor for conducting and directing magnetic lines of force to the outer rim of its cup shape, and
   a circular permanent magnet with magnetic poles at opposite ends thereof, embedded within said cup one magnetic pole of which is in contact with the base of said magnetic conductor and the other magnetic pole of which is covered by a magnetic insulator so that the magnetic field produced by said magnet is conducted only from said one contacted magnetic pole by said magnetic conductor directly to the outer rim of said cup each of said one contacted magnetic poles of each of said units being of opposite magnetic polarity from that of the other such that the respective outer rims have opposing polarity inducing an attractive flux path between the outer rims respectively of each of said magnetic conductors from one of the magnet units to the other.

10. In a denture retention device as in claim 9, wherein each of said magnet units include cup-shaped non-magnetic non-corrosive holder, said respective magnetic conductor and magnet are embedded within the associated holders in opposition to each other.

11. In a denture retention device as in claim 10, wherein one of said holders includes means on the extension of its base to non-rotatably lock the same to a denture to which it is attached.

12. In a denture retention device as in claim 10, the other of said magnet units being formed as a monolithic part of a dental post which has means thereon to thread the same into a tooth or other support for retention therein, and said holder of said dental post having means thereon for the threaded rotation of the dental post into the tooth or other support.

13. In a denture retention device as in claim 10, said magnets being permanent,
and said magnetic conductors being a ferromagnetic stainless steel.

14. In a denture retention device as in claim 10, said holder being of titanium.

15. A magnetic device for releasably retaining a denture to a tooth into which a dental post is threaded,
said device comprising an open ended non-magnetic non-corrosive denture holder containing a permanent magnet having opposed magnetic poles, one of which being directed to the open end of said denture holder, means for insulating said one magnet pole of said magnet with said other magnetic pole thereof being exposed, and magnetic conductor means filling said denture holder in contact with said exposed magnetic pole for conducting the magnetic flux from said exposed magnetic pole to the open end of said denture holder.

a dental post having threads and having an open ended holder of non-magnetic non-corrosive material and in which said dental post holder contains a permanent magnet having opposite magnetic poles one of which being directed to the open end of said post holder, means for insulating said one magnetic pole of said dental post magnet with the other magnetic pole thereof being exposed, said exposed magnetic pole of said dental post being of a magnetic polarity opposite to that of said exposed magnetic pole of said denture magnet, and magnetic conductor means filling said dental post holder in contact with said exposed magnetic pole of said dental post for conducting the magnetic flux from said exposed magnetic pole of the dental post to the open end of its respective holder, said magnetic conductor means of said holders of said denture and dental post forming a closed magnetic path therebetween and between their respective magnets to releaseably retain the denture to the dental post.

16. A magnetic device as in claim 15,
threads on said dental post and means on said dental post holder for threaded rotation of the dental post into a tooth,
and said denture holder having means to lock the same in the denture against displacement therefrom.

17. A magnetic device as in claim 16,
said holders and insulators being of titanium.

18. A magnetic device as in claim 16,
said magnetic conductor means being of ferromagnetic stainless steel.

19. A magnetic device as in claim 15,
each said magnetic conductor means being of substantially the same size and terminating in a ring shape at the open end of its respective holder.

20. A magnetic device as in claim 19,
rims on said ring shapes at which the magnetic flux paths of each of said magnetic conductor means are combined and completed in enlarged ring shapes.

21. The device according to claim 19 wherein said magnetically insulating means comprises a shaped body having a bottom surface covering the end of said magnet and a continuous integral side wall covering the corresponding side wall of said magnet.

* * * * *